United States Patent
Edwards et al.

(10) Patent No.: US 6,670,293 B2
(45) Date of Patent: *Dec. 30, 2003

(54) POROUS CALCIUM PHOSPHATE CEMENT

(75) Inventors: Brian Edwards, West Milford, NJ (US); Paul Higham, Ringwood, NJ (US); Joseph Zitelli, River Edge, NJ (US)

(73) Assignee: Howmedica Osteonics Corp., Allendale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/237,499

(22) Filed: Sep. 9, 2002

(65) Prior Publication Data

US 2003/0019396 A1 Jan. 30, 2003

Related U.S. Application Data

(63) Continuation of application No. 09/699,662, filed on Oct. 30, 2000, now Pat. No. 6,547,866.

(51) Int. Cl.$^7$ .......................... A61L 24/02; A61L 24/04; A61L 24/06
(52) U.S. Cl. ................. 501/84; 501/1; 106/35; 106/646; 623/23.62
(58) Field of Search .................. 501/84, 1; 106/35, 106/646; 623/23.62

(56) References Cited

U.S. PATENT DOCUMENTS

| | | |
|---|---|---|
| 4,880,610 A | 11/1989 | Constantz |
| RE33,161 E | 2/1990 | Brown et al. |
| RE33,221 E | 5/1990 | Brown et al. |
| 5,047,031 A | 9/1991 | Constantz |
| 5,149,368 A | 9/1992 | Liu et al. |
| 5,180,426 A | 1/1993 | Sumita |
| 5,336,264 A | 8/1994 | Constantz et al. |
| 5,342,441 A | 8/1994 | Mandai et al. |
| 5,409,982 A | 4/1995 | Imura et al. |
| 5,525,148 A | 6/1996 | Chow et al. |
| 5,820,632 A | 10/1998 | Constantz et al. |

FOREIGN PATENT DOCUMENTS

| | | | |
|---|---|---|---|
| JP | 51071896 | | 6/1976 |
| JP | 6-30985 | * | 2/1994 |
| JP | 06-030985 | | 2/1994 |
| JP | 10036106 | | 2/1998 |

* cited by examiner

Primary Examiner—C. Melissa Koslow
(74) Attorney, Agent, or Firm—Lerner, David, Littenberg, Krumholz & Mentlik, LLP

(57) ABSTRACT

A kit and a method for making a porous cement which self sets to hydroxyapatite and has an interconnected porosity is produced by mixing a calcium source and a phosphate source with a carbonate source and mixing this powdered component with a liquid component having an acid component. The liquid component comprises water or an aqueous solution containing an acid. The acid and the carbonate react to form carbon dioxide thereby producing an interconnected porosity in the normally solid self-hardening bone cement. The method requires only a relatively low weight percent of the acid and base to be mixed with the liquid and powder cement components.

14 Claims, 1 Drawing Sheet

POROUS CALCIUM PHOSPHATE CEMENT

CROSS-REFERENCE TO RELATED APPLICATIONS

The present application is a continuation of U.S. Ser. No. 09/699,662 filed Oct. 30, 2000 now U.S. Pat. No. 6,547,866.

BACKGROUND OF THE INVENTION

This invention relates to calcium phosphate cements which set after the mixing of a powdered calcium and phosphate source in an aqueous solution to form hydroxyapatite (HA). More particularly, it relates to the addition of citric acid and sodium bicarbonate to produce carbon dioxide during the setting of a calcium phosphate cement, thereby introducing macroporosity into the structure.

It is sometimes desired that bone cements and bone filler materials which harden or set have an interconnected porosity (macroporosity) throughout their structure after hardening. This interconnected porosity, if of sufficient pore size, allows for vascularization and tissue ingrowth to occur into the structure. Pores greater than 70 microns in diameter have been found to allow tissue ingrowth. This tissue ingrowth can be encouraged by coating or filling the pores with osteoinductive or osteoconductive factors such as bone morphogenic proteins (BMPs). Such factors are well known to those skilled in the art. Other therapeutic agents such as antibiotics or chemo-therapeutic agents may be introduced into the porosity by adding them to the liquid or powder.

In the past, porosity has been generated by including fillers which are soluble in physiological fluids or which are resorbed after implantation. These systems have the disadvantage that the porosity only occurs after implantation and thus the pores cannot be filled with growth factors or other therapeutic agents prior to implantation. In addition, to form the required interconnected porosity, up to 50 volume percent of resorbable filler must be added to the calcium and phosphate source precursor powdered material. This sometimes adversely affects material properties and reduces the amount of hydroxyapatite formed in the reaction of the calcium and phosphate precursors.

Also, foaming agents, such as citrimide BP which reduce the surface tension of the water have been used. However, this produces unwanted ammonium compounds when used in vivo.

U.S. Pat. No. 5,820,632 to Constantz et al. relates to a calcium phosphate cement wherein when a porous structure is desired, various additives may be included which may be leached out so as to provide for porosity in the cement. This porosity is in addition to any porosities achieved with a release of gas formed during the reaction to produce the product. Constantz et al. teaches including aggregates of soluble materials generally above 25 volume percent to develop sufficient interconnected porosity to foster bony ingrowth with the volume of aggregate normally being less than 50 volume percent. Specifically, Constantz et al. suggests the addition of calcium chloride and sodium or potassium hydroxide which are water soluble and will be leached out to provide the porosity.

U.S. Pat. No. 5,525,148 to Chow et al. teaches the use of pore forming agents that are preferably, substantially insoluble in the cement itself and can be removed by either resorbtion into body tissue, dissolution into physiological solutions, dissolution in solvents or heating after the cement has hardened. The pore forming agents taught by Chow et al. include sugar, sodium bicarbonate and phosphate salts.

Thus, there is a need to find a simple way of forming an interconnected porosity of sufficient pore size during cement hardening or setting and which avoids adding large amounts of filler to the cement. It has been found that the production or introduction of sufficient amounts of carbon dioxide gas during the reaction of the calcium and phosphate precursors to form HA produces the desired porosity.

It has been found that adding sodium bicarbonate and citric acid to the calcium and phosphate precursors to the formation of hydroxyapatite with a ratio of these acid and alkaline components selected such that the final result of their reaction does not change the pH of the aqueous solution, that a final cement having the desired porosity, sufficient hydroxyapatite and sufficient physical properties are produced.

SUMMARY OF THE INVENTION

It is an object of this invention to provide a method of preparing calcium phosphate cement compositions, which self-hardens substantially to hydroxyapatite at ambient temperatures when in contact with an aqueous medium, comprising, combining one or more sparingly soluble calcium phosphates along with an acid and base to produce a set material having an interconnected porosity.

It is another object of the invention to provide an acid and base which react to form carbon dioxide during the setting process of the calcium phosphate cement compositions and which does not alter the final pH of the mixture of the one or more sparingly soluble calcium phosphate powders when combined with the aqueous medium normally added thereto.

These and other objects of the invention are provided by a method for making a porous cement which sets to hydroxyapatite at ambient temperatures comprising mixing a powder comprising a calcium source, a phosphate source and a base with a liquid comprising an aqueous solution containing an acid wherein the calcium source and the phosphate source mix with the liquid component to form hydroxyapatite and the acid and base react to form carbon dioxide producing an interconnected porosity in the material. In the preferred embodiment, the base is a carbonate selected from the group consisting of sodium carbonate, sodium bicarbonate, calcium carbonate and calcium bicarbonate or a combination thereof. The preferred acid is selected from the group consisting of citric acid, malic acid, fumaric acid, lactic acid, succinic acid and orthophosphoric acid or a combination thereof.

The preferred calcium and phosphate sources may be selected from the group consisting of tetra-calcium phosphate, dicalcium phosphate, tricalcium phosphate and monocalcium phosphate. The chosen calcium and phosphate sources must self-set when coming into contact with an aqueous solution. This requires a combination or more calcium and/or phosphate sources. Thus, one source may be calcium alone or phosphate alone or one source may be a compound having both calcium and phosphate. The preferred ratio of acid to carbonate to produce a neutral pH has been found to be about 0.7 grams of acid to about 1.0 grams of carbonate. The preferred ratio of the acid and carbonate to the combined powdered and liquid components forming the calcium phosphate cement is about 10 to 20% by weight.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings wherein similar reference characters denote similar elements throughout the several views, in which.

DESCRIPTION OF THE PREFERRED EMBODIMENTS

This invention relates to calcium phosphate cements of the type taught in Brown and Chow, U.S. reissued Pat. No. RE 33,161 and U.S. Pat. No. RE 33,221 and in Chow and Takagi U.S. Pat. No. 5,525,148 and in Constantz U.S. Pat. No. 4,880,610, the teachings of which are incorporated herein by reference.

The method for porosity generation of the present invention is the addition of citric acid monohydrate in an aqueous mixture and sodium bicarbonate in powder form into the calcium phosphate powder mixture taught by the patents referred to above in which tetra-calcium phosphate and dicalcium phosphate powders are mixed with a liquid component which may be water, dionized water or an aqueous sodium phosphate solution made with water or dionized water. In the preferred embodiment, the ratio of acid to base is 1.0 gram of a base such as sodium bicarbonate to 0.7 grams of an acid such as citric acid. In the preferred embodiment, the sodium bicarbonate powder is mixed with the tetra-calcium phosphate and dicalcium phosphate powders with the resultant mixture then being combined with an aqueous liquid into which the citric acid has been added as a liquid. The preferred liquid to powder ratio is between about 0.25 to 0.35. The preferred weight percent of the acid/base to the liquid and powder combination is between about 10 to about 20 weight percent.

EXAMPLE

The ratio of acid to base (citric acid to sodium bicarbonate) was determined by reacting various ratios of each component in 10 ml of water. The ratio that left the pH of the water unchanged after completion of the reaction was chosen to be mixed with the powdered tetra-calcium phosphate and dicalcium phosphate combination. It was determined that the ratio of 0.7 grams of citric acid to 1.0 grams of sodium bicarbonate produced a neutral pH.

Sodium bicarbonate was mixed as a powder into the powdered tetra-calcium phosphate and dicalcium phosphate. Citric acid monohydrate was mixed into the deionized water liquid component. The acid/base ratio (A/B) was 0.7 grams of citric acid to 1.0 grams of sodium bicarbonate. A series of tests were performed in which the citric acid was added to deionized water and also was added to a 0.25 M sodium phosphate solution. Various liquid/powder (l/p) ratios were evaluated. Although the acid used was in solution, the invention would work equally well if an acid in dry form (free of uncombined water) was used as part of the powdered component.

Figure 1:
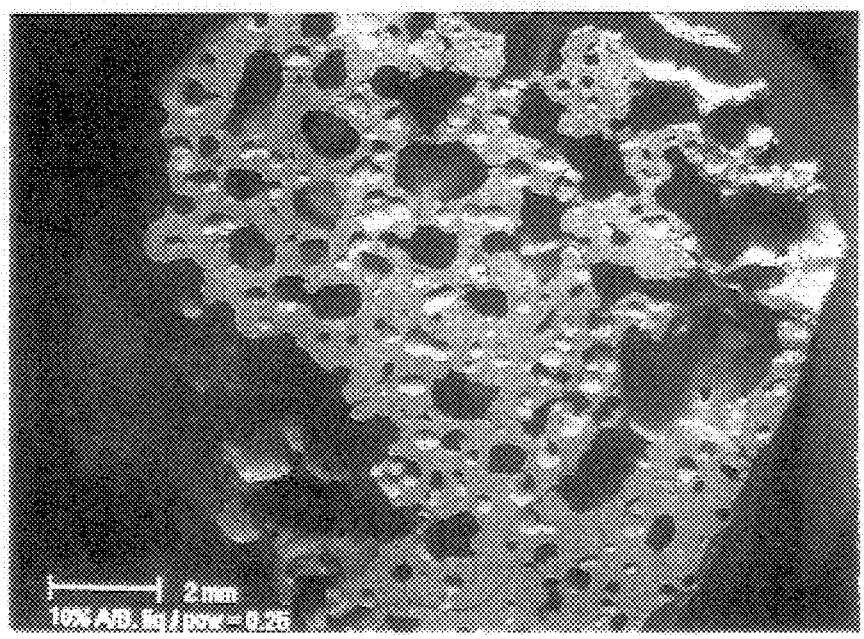
FIG. 1 is a cross-sectional micrograph of the porous bone cement of the present invention formed at liquid to powder ratio of 0.25 and an acid/base weight percent of 10%.
Figure 2:
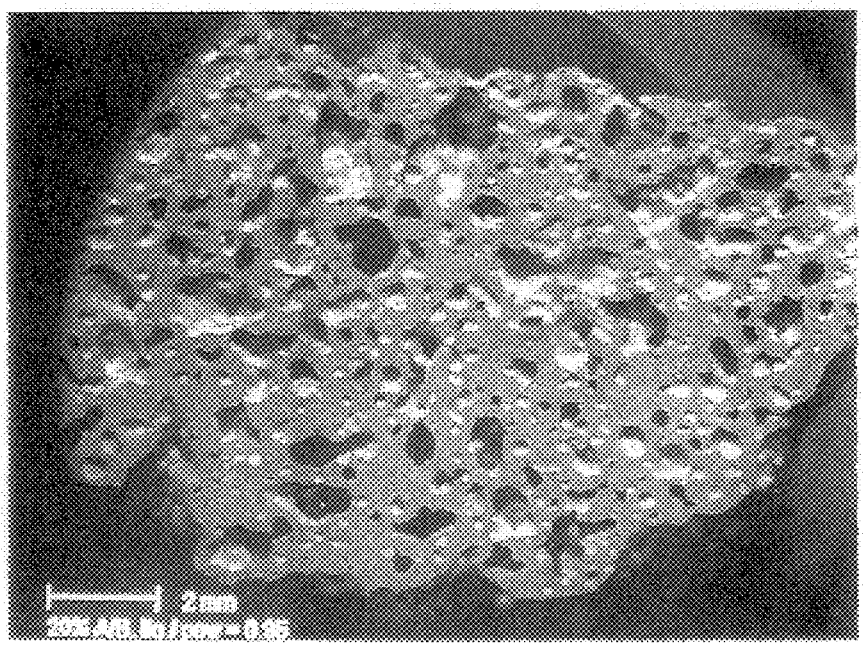
FIG. 2 is a cross-sectional micrograph of the porous bone cement of the present invention made from a liquid to powder ratio of 0.35 and an weight percent of acid to base of 20%.

After twenty-four (24) hours of setting at 37° C. in greater than 95% relative humidity, each cement specimen was dried to stop the reaction. X-ray diffraction measurements were made to determine the percent conversion to hydroxyapatite (HA) and the cement was sectioned to reveal the porosity. FIGS. 1 and 2 show the sections of two samples for illustrative purposes only.

The results of those tests are summarized in Table I. From this table, it can be seen that the specimen number 10 and specimen number 11 produced the most acceptable levels of hydroxyapatite of 67 and 69%, respectively and greater than 35% porosity. The pore sizes were between 440 and 580 microns. Pore sizes of at least 70 microns are desirable. Specimen 10 include a liquid to powder to ratio of 0.35 and 20% by weight of the citric acid and sodium bicarbonate added in with the aforementioned ratio of 0.7 grams of the citric acid to every gram of sodium bicarbonate and had a 35% porosity with 67% HA. Likewise, specimen 11 which utilized a 0.25 liquid to powder ratio and a 10% acid base weight ratio produced a 47% porosity with 69% HA.

While the Example deals with a calcium phosphate bone material, the method of producing a porous structure in a bone cement or filler could be utilized on any bone cement type such as a glass ionomer cement, poly (propylene fumarate) or a methacrylate cement where liquid and powdered components are mixed. A methacrylate cement is made by reacting a liquid methacrylate monomer with a powdered methacrylate polymer. Again, the powdered sodium bicarbonate is added to the powdered component and an acid source, such as citric acid, is added to the liquid component. Also, any gas producing chemical reaction could be used to form the pores. Rather than having the acid in the liquid component, it is possible to add the acid in a crystalline form as a solid component. An example of such an acid material is phosphoric acid free of uncombined water.

It is also possible to introduce carbon dioxide, nitric oxide and a combination thereof or an inert gas such as nitrogen or helium directly into the setting cement mixture to form the porosity. This can be accomplished through a port in the mixing container.

TABLE I

| Cements Mixed Using Deionized Water | | | | |
|---|---|---|---|---|
| specimen # | l/p | wt % A/B in mix | % porosity | % converted to HA | comments |
| 1 | 0.125 | 20 | 12 | 31 | |
| 2 | 0.188 | 5 | 13 | — | 109 μm aps* |
| 3 | 0.188 | 20 | 20 | 45 | |
| 4 | 0.25 | 2 | 8 | 37 | |
| 5 | 0.25 | 5 | 36 | 50 | 580 μm aps* |
| 6 | 0.35 | 10 | 36 | 64 | |
| 7 | 0.25 | 20 | 32 | 55 | 440 μm aps* |
| 8 | 0.25 | 30 | 51 | 66 | |
| 9 | 0.25 | 40 | 51 | 63 | |
| Cements Mixed With Sodium Phosphate Solution | | | | |
| specimen # | l/p | wt % A/B in mix | % porosity | % converted to HA | |
| 10 | 0.35 | 20 | 35 | 67 | |
| 11 | 0.25 | 10 | 47 | 69 | |
| 12 | 0.30 | 10 | 26 | 58 | |

*aps = average poresize

The calcium phosphate materials mixed without the gas forming citric acid sodium bicarbonate components had a macroporosity of only 4%.

The pore size can be controlled by using less liquid in the liquid to powder ratio and/or less of the acid-base mixture to obtain smaller pore sizes. Conversely, more liquid or a higher weight percent of acid-base results in more porosity and larger pores. FIGS. 1 and 2 show the porous bone cements of Examples 11 and 10 respectively, showing average pore sizes greater than 70 microns.

While several examples of the present invention have been described, it is obvious that many changes and modifications may be made thereunto, without departing from the spirit and scope of the invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A kit for producing a self-setting bone cement comprising:
    water;
    an acid source selected from the group consisting of citric acid, malic acid, phosphoric acid, fumaric acid, lactic acid, succinic acid and a combination thereof; and
    a powdered composition containing at least two powdered components mixed together, at least one component containing a calcium phosphate source and at least one component containing a phosphate source, said at least two powdered components capable of reacting with said water to form said self-setting bone cement and said mixed at least two powdered components containing a carbonate selected from the group consisting of sodium carbonate, sodium bicarbonate, calcium carbonate, calcium bicarbonate and a combination thereof, wherein the ratio of the weights of the acid source to the carbon are chosen such that the final result of their reaction does not change the final pH of the mixture of the at least two powdered components and water with the ratio of acid to the weight of carbonate being about 0.7.

2. The kit as set forth in claim 1, wherein the weight ratio of the acid and carbonate to the combined water and at least two powdered components forming the cement is about 10 to 20%.

3. The kit as set forth in claim 1, wherein the acid and water are supplied as a mixture in the kit.

4. A method for making a porous cement which self sets to hydroxyapatite as the predominant product at ambient temperatures comprising:
    mixing powdered components at least one being a calcium source and at least one being a phosphate source and at least one powdered component being a carbonate selected from the group consisting of sodium carbonate, sodium bicarbonate, calcium carbonate, calcium bicarbonate and a combination thereof to form a powdered mixture, the calcium source and the phosphate source capable of reacting with water to form the self-setting cement;
    mixing a liquid component comprising water and an acid; and
    mixing said powdered mixture and said liquid component causing said acid and carbonate to react to form a gas and causing said calcium and phosphate sources to react with water to form the self-setting hydroxyapatite cement wherein the ratio of the weights of acid to the carbonate is chosen such that the final result of their reaction does not change the final pH of the mixture of the powder and water with the ratio of the weight of acid to carbonate being about 0.7.

5. The method as set forth in claim 4, wherein the carbonate is selected from the group consisting of sodium carbonate, sodium bicarbonate, calcium carbonate, calcium bicarbonate and a combination thereof.

6. The method as set forth in claim 5, wherein the acid is selected from the group consisting of citric acid, malic acid, phosphoric acid, fumaric acid, lactic acid, succinic acid and a combination thereof.

7. The method as set forth in claim 6, wherein said acid and carbonate react to form carbon dioxide.

8. The method as set forth in claim 7, wherein the gas produces a cement having an average pore size of at least 70 microns after setting.

9. The method as set forth in claim 8, wherein the gas produces a cement having an average pore size of between 440 microns and 580 microns after setting.

10. The method of claim 4, wherein the weight ratio of the acid and carbonate to the water and powdered mixture forming the cement is 10% to 20%.

11. A bone treatment material comprising:
    an acid source selected from the group consisting of citric acid, malic acid, phosphoric acid, fumaric acid, lactic acid, succinic acid and a combination thereof; and
    a powdered combination containing at least two powdered calcium phosphate mineral components mixed together, said at least two powdered calcium phosphate components capable of reacting with said water to form said self-setting bone cement and said mixed at least two powdered calcium phosphate components containing a carbonate selected from the group consisting of sodium carbonate, sodium bicarbonate, calcium carbonate, calcium bicarbonate and a combination thereof, wherein the ratio of the weights of the acid to the carbonate are chosen such that the final result of their reaction does not change the final pH of the mixture of the at least two powdered components and water.

12. The bone treatment material as set forth in claim 11, wherein said acid and carbonate react to form carbon dioxide gas.

13. The bone treatment material as set forth in claim 11, wherein the gas produces a cement having an average pore size of at least 70 microns after setting.

14. The bone treatment material as set forth in claim 11, wherein the gas produces a cement having an average pore size of between 440 microns and 580 microns after setting.

* * * * *

UNITED STATES PATENT AND TRADEMARK OFFICE
CERTIFICATE OF CORRECTION

PATENT NO.     : 6,670,293 B2
DATED          : December 30, 2003
INVENTOR(S)    : Brian Edwards, Paul Higham and Joseph Zitelli It is certified that error appears in the above-identified patent and that said Letters Patent is hereby corrected as shown below:

Column 5,
Line 38, "carbon" should read -- carbonate --.

Signed and Sealed this

Sixth Day of July, 2004

JON W. DUDAS
*Acting Director of the United States Patent and Trademark Office*